United States Patent
Fleischer et al.

(10) Patent No.: US 7,992,426 B2
(45) Date of Patent: Aug. 9, 2011

(54) APPARATUS AND METHOD FOR INCREASING THE SELECTIVITY OF FET-BASED GAS SENSORS

(75) Inventors: Maximilian Fleischer, Höhenkirchen (DE); Uwe Lampe, Buxtehude (DE); Hans Meixner, Haar (DE); Roland Pohle, Herdweg (DE); Ralf Schneider, München (DE); Elfriede Simon, München (DE)

(73) Assignee: Micronas GmbH, Freiburg (DE)

( * ) Notice: Subject to any disclaimer, the term of this patent is extended or adjusted under 35 U.S.C. 154(b) by 615 days.

(21) Appl. No.: 11/587,171

(22) PCT Filed: Apr. 21, 2005

(86) PCT No.: PCT/EP2005/004281
§ 371 (c)(1),
(2), (4) Date: Feb. 18, 2009

(87) PCT Pub. No.: WO2005/103680
PCT Pub. Date: Nov. 3, 2005

(65) Prior Publication Data
US 2009/0211437 A1 Aug. 27, 2009

(30) Foreign Application Priority Data
Apr. 22, 2004 (DE) .......................... 10 2004 019 640

(51) Int. Cl.
*G01N 33/00* (2006.01)
*G01N 27/414* (2006.01)
(52) U.S. Cl. ............................ 73/31.06; 96/117; 96/139
(58) Field of Classification Search .................... 96/115, 96/117, 117.5, 139, 143, 146, 153, 413; 95/90, 95/148; 73/23.2, 31.06
See application file for complete search history.

(56) References Cited

U.S. PATENT DOCUMENTS

| 3,663,870 A | 5/1972 | Tsutsumi et al. |
| 4,023,549 A | 5/1977 | Hewitt |
| 4,151,060 A | 4/1979 | Isenberg |

(Continued)

FOREIGN PATENT DOCUMENTS
DE 2947050 11/1979
(Continued)

OTHER PUBLICATIONS

Machine generated English translation of EP 1104884 A, published Jun. 2001.*

(Continued)

*Primary Examiner* — Frank M Lawrence
(74) *Attorney, Agent, or Firm* — Muncy, Geissler, Olds & Lowe, PLLC

(57) ABSTRACT

A FET gas sensor having a relatively low operating temperature, for example, room temperature, is free from cross sensitivities from interfering gases by a preceding in-line filter. The sensor's service life is substantially stabilizable by using fabric-like activated charcoal filters which can be regenerated by a moderate temperature increase, and by limiting the diffusion of the analyte gas, which is made possible by the relatively small amount of gas detectable on the sensitive layer of the sensor. This substantially increases the service life of the filters. The gas sensor eliminates cross sensitivities to thereby increase the detection reliability thereof. Also, the gas sensor has relative long term stability and is economical to build. The gas sensor can read relatively weak signals generated by gas-sensitive layers, for example, without other stronger gas signals interfering with the weak signals.

21 Claims, 2 Drawing Sheets

U.S. PATENT DOCUMENTS

| | | | | |
|---|---|---|---|---|
| 4,354,308 | A | 10/1982 | Shimada et al. | |
| 4,633,704 | A | 1/1987 | Tantram et al. | 73/23 |
| 4,638,346 | A | 1/1987 | Inami et al. | |
| 4,792,433 | A | 12/1988 | Katsura et al. | |
| 5,635,628 | A | 6/1997 | Fleischer et al. | |
| 5,879,527 | A | 3/1999 | Kiesele et al. | 204/431 |
| 6,041,643 | A | 3/2000 | Stokes et al. | |
| 6,454,834 | B1 | 9/2002 | Livingstone et al. | 95/11 |
| 6,566,894 | B2 | 5/2003 | Rump | |
| 6,703,241 | B1 * | 3/2004 | Sunshine et al. | 436/8 |
| 6,935,158 | B2 | 8/2005 | Serina et al. | |
| 7,279,132 | B2 * | 10/2007 | Sultan et al. | 422/83 |
| 7,707,869 | B2 * | 5/2010 | Fleischer et al. | 73/31.05 |
| 2002/0092974 | A1 | 7/2002 | Kouznetsov | 250/222.2 |
| 2004/0112764 | A1 | 6/2004 | Stokes et al. | |
| 2004/0133116 | A1 | 7/2004 | Abraham-Fuchs et al. | |
| 2005/0035808 | A1 | 2/2005 | Frerichs | |
| 2005/0042133 | A1 * | 2/2005 | Staphanos | 422/50 |

FOREIGN PATENT DOCUMENTS

| | | | |
|---|---|---|---|
| DE | 4028062 | 9/1990 | |
| DE | 4105598 | 9/1992 | 27/14 |
| DE | 4239319 | 4/1993 | |
| DE | 4333875 | 4/1995 | |
| DE | 19534557 | 3/1997 | 27/12 |
| DE | 19613274 | 10/1997 | |
| DE | 197 08 770 | 8/1998 | 27/12 |
| DE | 10245947 | 4/2004 | |
| EP | 0952447 | 4/1998 | 27/12 |
| EP | 0 947 829 | 10/1999 | |
| EP | 1 059 528 | 5/2000 | 27/414 |
| EP | 1059528 | 5/2000 | 27/414 |
| EP | 1 104 884 | 11/2000 | 27/414 |
| EP | 1104884 | 11/2000 | 27/414 |
| EP | 1103809 | 5/2001 | |
| EP | 1 176 418 | 1/2002 | |
| JP | 01059049 | 3/1989 | |
| JP | 03131749 | 6/1991 | |
| JP | 03259736 | 11/1991 | |
| WO | WO 94/23288 | 10/1994 | |
| WO | WO 96/01992 | 1/1996 | |
| WO | WO 98/41853 | 9/1998 | |
| WO | WO 03/050526 | 6/2003 | |

OTHER PUBLICATIONS

Fleischer et al., "Selective gas detection with high-temperature operated metal oxides using catalytic filters," Sensors and Actuators B, vol. 69, pp. 205-210, 2000.

Kienle et al., "Aktivkohle and ihre industrielle Anwendung," Stuttgart : Enke, ISBN 3-432-90881-4, pp. 126 and 162, 1980.

Müller et al., "Adsorber für geringe Lösemittel-beladung," Intelligente Abluftreinigung mit Strom, Verfahrenstechnik, vol. 37, No. 9, pp. 30-31, 2003.

CCI Charcoal International : Aktivkohletextilien erhalten einheitlichen Markennamen Zorflex, MaschinenMarkt, 2004, No. 17, p. 89.

Kienle et al., "Acticated Charcoal and its Industrial Application," Stuttgart : Enke, ISBN 3-432-90881-4, pp. 126 and 162-163, 1980.

Müller et al., "Adsorber for a Low Solvent Load," Intelligent Exhaust Air Cleaning Using Electric Current, Verfahrenstechnik, vol. 37, No. 9, pp. 30-31, 2003.

CCI Charcoal International : Activated Charcoal Textiles Given Uniform Brand Name of Zorflex, MaschinenMarkt, 2004, No. 17, p. 89. Verifications of Translation.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Gergintschew et al., "The capacitively controlled field effect transistor (CCFET) as a new low power gas sensor," Sensors and Actuators B: Chemical, Elsevier Sequoia, vol. 36, No. 1, Oct. 1996, pp. 285-289.

Pohle et al., "Realization of a New Sensor Concept: Improved CCFET and SGFET Type Gas Sensors in Hybrid Flip-Chip Technology," Transducers, 12$^{th}$ International Conference on Solid-State Sensors, Actuators and Microsystems, Jun. 2003, vol. 1, 9, pp. 135-138.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Covington, et al. "Combined smart chemFET/resistive sensor array," Proceedings of the IEEE, vol. 2., pp. 1120-1123, 2003.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

M. Lehmann, "Nanometre Dimensions in Bio and Gas Sensor Technology", MST News, Mar. 2004, pp. 43-47, XP-002379751.

* cited by examiner

APPARATUS AND METHOD FOR INCREASING THE SELECTIVITY OF FET-BASED GAS SENSORS

PRIORITY INFORMATION

This patent application claims priority from International patent application PCT/EP2005/004281 filed Apr. 22, 2005 and German patent application 10 2004 019 640.0 filed Apr. 22, 2004, which are hereby incorporated by reference.

BACKGROUND INFORMATION

This invention relates in general to gas sensors and in particular to a device for increasing the selectivity of gas sensors that employ field effect transistors ("FETs").

FIGS. 3 and 4 herein and German Patents DE 4239319, DE 19956744, and DE 19956806 disclose FET gas sensors of hybrid construction, which read the work function of a gas-sensitive material using a field effect transistor. These sensors have a number of different applications. On the one hand, they can be operated at ambient temperature, or at slightly elevated temperatures, and they therefore permit low-power operation with batteries or direct connection to data bus lines without the use of auxiliary power. On the other hand, a large number of different materials can be used as detection materials with this sensor structure, so that a previously unachieved bandwidth of gases can be detected with these sensors. Economical manufacture is possible with readily automated techniques because of their simple structure. Since the control electronics can be integrated into the Si chip with little added cost, the costs of gas sensor systems having the control electronics are lower than for other sensor technologies.

These gas sensors are also subject to the problems of cross sensitivities; in other words, other gases that exist in the application can cause interference with the sensor signal. That is, the sensor reacts to interfering gases that may distort a concentration of the measured gas (i.e., direct cross sensitivity). Similarly, sensitivity to the target gas can be modified by the presence of an interfering gas (i.e., indirect cross sensitivity). Both effects lead to distortion of the desired sensed values and can impair or even prevent usability in an application, depending on the requirement profile.

A first approach to eliminating existing drawbacks is an intelligent signal processor on the system level. In this case, the attempt is made to eliminate the consequences of incorrect measurements by a plausibility consideration for the sensor signal, for example. This approach is not possible with indirect cross sensitivity.

A second approach uses an additional sensor element that is sensitive to the target gas and corrects the indicated value of the primary sensor element with this auxiliary information from the additional sensor element during the test. This is an approach that was actually pursued with array-capable sensors (multiple system) like GasFETs; see for example German Patent DE 19956806. This variant is always associated with distinctly greater effort and higher cost. The consequences of indirect cross sensitivity, however, cannot be eliminated with this approach, or only with great effort, for example with large sensor arrays or extensive calibration models.

A third approach comprises further developing and optimizing the sensor material so that selective detection of the target gas is achieved. This can be achieved for some specific applications, for example see German Patents DE 19926747, DE 19849932, and DE 19708770. However, it cannot be assumed from this that this is possible for most detection tasks.

A fourth approach of the prior art is related directly to the FET gas sensors, for example see German Patent DE 19849932. It utilizes the geometry of this structure to produce very high electric field strengths on the surface of the sensor layer by applying manageable voltages, for example 10V, to the suspended gate electrode because of the small air gap. These affect the adsorption properties of the detected molecules. The influence of an interfering gas can be eliminated by comparing the measured signals with various electric field strengths on the surface of the sensor layer. This approach is not universally applicable, such that its utility is limited to a few special cases.

A fifth prior art approach constitutes a self-explanatory procedure for eliminating cross sensitivities. The use of filters that are mounted between the gas mixture to be detected and the gas sensor is proposed for this purpose. They are permeable to the target gas but do not allow gases that cause cross sensitivities to reach the sensor. Exemplary embodiments in this case are catalytic filters as disclosed in German Patent DE 19926747, with the concentrations of interfering gas being actively removed by a chemical reaction. Gas sensors based on heated, semiconducting metal oxides are often combined with an activated charcoal filter. This removes gases that cause cross sensitivities by adsorbing them on the large internal surface area of the filter material, but with the target gas being allowed to pass through the filter and be detected by the sensor. A widely used example of such sensors is gas sensors for detecting toxic gases, CO for example, or explosive gases, for example escaping natural gas/$CH_4$ in domestic atmospheres. Alcohol vapors occurring in the household often interfere with their measurement signals as disclosed in German Patent DE 19926747. Filters are also used frequently for electrochemical gas sensors. Activated charcoal is a very good absorber for alcohol vapors, for example, in long-term operation in these applications. However, the filter can become saturated, so that the filter loses its activity and the interfering gas ultimately does reach the sensor and is detected.

There is a need for a FET-based gas sensor that prevents distortion of the measured signal by cross sensitivities.

SUMMARY OF THE INVENTION

The invention is founded on the recognition that FET-based gas sensors that have a very low operating temperature in contrast with the prior art, for example room temperature, and that are freed of cross sensitivities from interfering gases by preceding in-line filters, are substantially stabilizable with regard to the service life of a sensor. This is accomplished by using fabric-like activated charcoal filters that can be regenerated by a moderate temperature increase, and by limiting the diffusion of the analyte gas, which is made possible by the extremely small amount of gas detectable on the sensitive layer of an FET gas sensor. This is able to substantially increase the service life of filters.

Advantageously, the sensor effectively eliminates cross sensitivities to increase the detection reliability of gas sensors. In addition, the sensor has long term stability and is relatively economical to build. The sensors make it possible to read weak signals generated by gas-sensitive layers, for example, without the ability of any other stronger gas signals to interfere with the weak signals. Such sensors have operating temperatures between room temperature and about 100° C.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
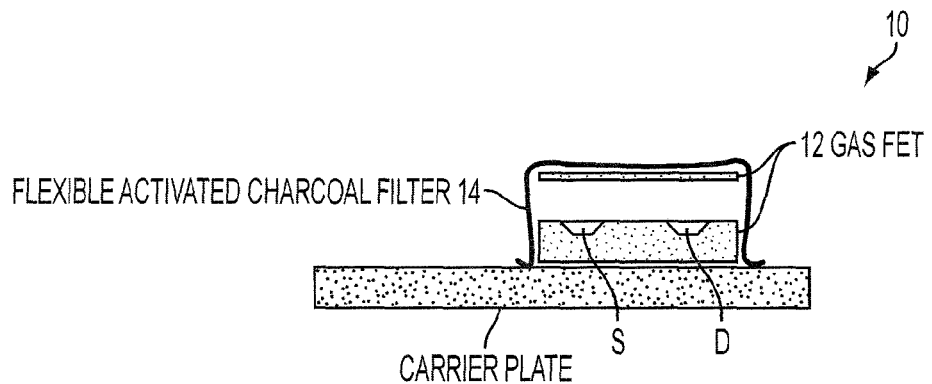
FIG. 1 is a cross-sectional illustration of a GasFET with a flexible activated charcoal filter mounted according to the invention with no separation.

FIG. 1 is a cross sectional illustration of a sensor system 10 of a GasFET 12 that includes a Si base with source, drain, and channel regions with a suspended gate electrode. The GasFET includes a flexible activated charcoal filter 14 mounted with no separation according to the invention, which encloses the entire sensor system.

Figure 2:
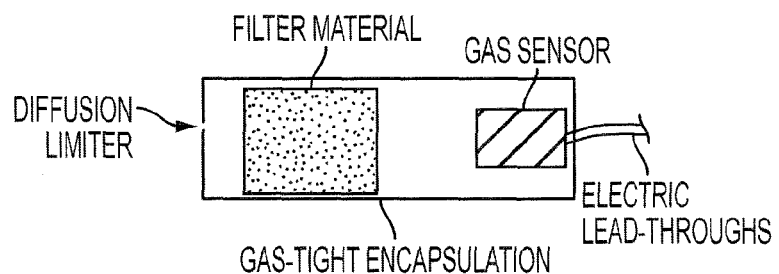
FIG. 2 is a schematic illustration of the structure for slowing filter saturation by limiting the entry of gas.

FIG. 2 schematically illustrates a structure for slowing filter saturation by limiting the entry of gas, so that the filter has a substantially longer service life.

Figure 3:
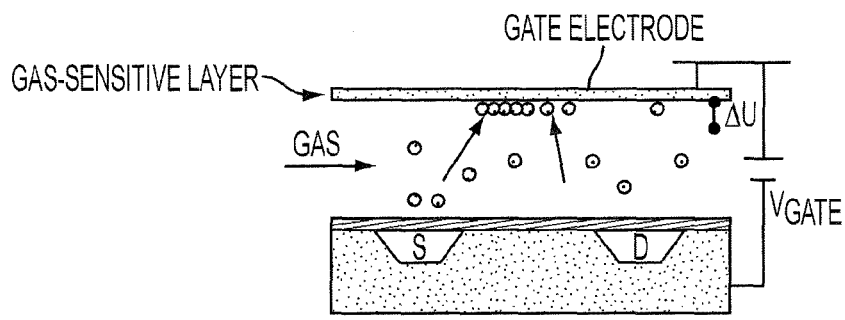
FIG. 3 is a cross-sectional schematic illustration of a prior art GasFET having a suspended gate.

FIG. 3 is a cross-sectional schematic illustration of a prior art GasFET that includes a suspended gate FET (SGFET).

Figure 4:
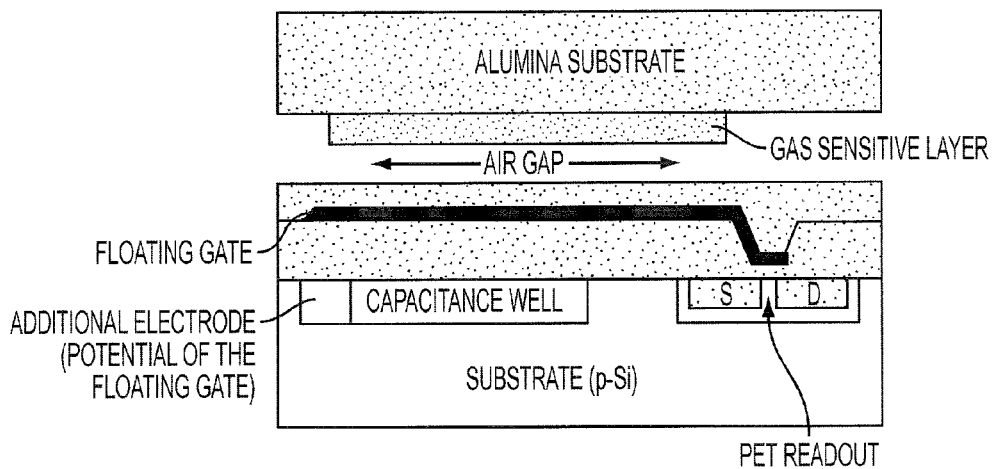
FIG. 4 is a cross-sectional schematic illustration of a prior art GasFET having a capacitively coupled FET.

FIG. 4 is a cross-sectional schematic illustration of a prior art GasFET that includes a capacitively coupled (CCFET).

Figure 5:
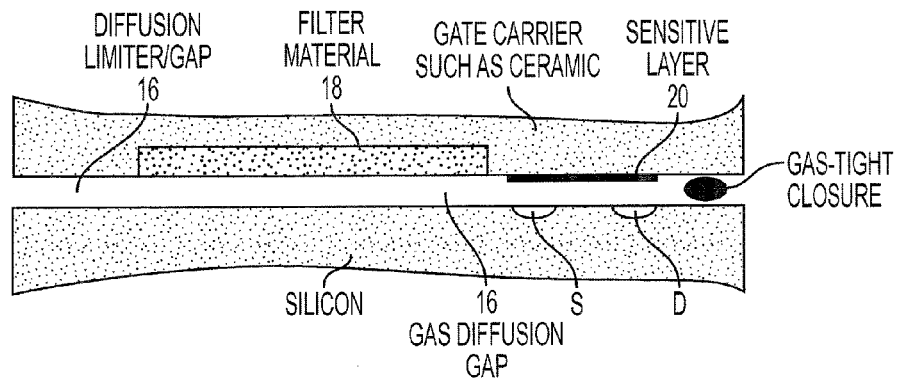
FIG. 5 is a cross-sectional illustration of a gas sensor in which the gas filter is mounted in a depression in the ceramic.

FIG. 5 is a cross-sectional illustration of a gas sensor that includes a diffusion gap 16 to limit the diffusion.

Two embodiments shall now be discussed.

A first embodiment uses the property of GasFETs that their operating temperatures are drastically lower than those of heated metal oxide sensors, and typically lie between room temperature and about 100° C. In this embodiment, a filter 14 is mounted at only a slight physical distance from the actual sensor element. FIG. 1 illustrates a typical structure. Inasmuch as the operating temperature of the GasFET is about 100° C. at most, as mentioned above, the filter 14 can assume the operating temperature of the GasFET without an unacceptable decrease in its adsorbent activity.

A suitable filter material is carbon fiber fabric, for example that sold by Charcoal Cloth under the trade name Zorflex™. The fabric is made from pure viscose cellulose that is completely carbonized under appropriate reaction conditions. Because of its structure, the material is distinguished by a large active surface area, with the active surface being produced essentially by the micropores within the fibers. Other properties are high mechanical flexibility and stability, low weight, and high chemical resistance. Since the filters are made as a fabric before carbonization, the properties can be varied over a wide range, for example by fiber length and thickness, fabric structure, fabric strength, etc. The adsorption of gas is described as pure physical adsorption. Because of this, the material can be regenerated by the desorption of all adsorbates by raising the temperature by 100° C., for example. Specific impregnations distinctly increase the filtering activity for certain acidic or basic gases. These gases are then bound by chemisorption. Such fabrics are used successfully, for example, as a protective lining, for water purification, as oil filters for purification of compressed air, to protect works of art against corrosive gases, and as filters in gas masks.

The GasFET sensors are usually equipped with a heating element to stabilize the temperature. This heating element is now used according to an aspect of the invention to heat the structure, the gas sensor with the filter 14 mounted directly on it, to a temperature higher than the operating temperature. Typical temperatures are in the range of 200-300° C. Because the filter 14 and the sensor are in direct contact with one another, there is strong heat transfer from the GasFET 12 to the filter 14, and the latter reaches the temperature of the gas sensor. There is outgassing of the activated charcoal filter from the thermal activation at this temperature. The adsorbed gases leave the filter, so that its complete adsorption capacity is recovered (i.e., the filter is regenerated). Typical periods for performing the regeneration process are from 1 to 20 days. It typically takes from 0.5 to 3 minutes to accomplish this regeneration process. No predictive sensor signal must be expected from the gas sensor during the regeneration process, both because the GasFET 12 is being operated at too high a temperature, and because a certain amount of the interfering gas can also reach the GasFET 12 due to the compelled desorption.

In addition, the measurement signal can be used during the regeneration process to monitor the process. Inasmuch as the interfering gases escaping from the filter usually cause a significant sensor reaction, even at the elevated operating temperatures, there is a sensor deflection attributed to the progress of the regeneration process. This can be used to monitor when the regeneration process has been completed.

A second embodiment is based both on structural details of the FET gas sensors and on their property of needing only a very small amount of analyte gas for detection, in contrast to the highly gas-consuming metal oxide sensors. To lengthen the service life of the filter elements and to prevent deactivation from saturation, gas access to the filter element is sharply limited. This greatly delays filter saturation. However, the small amount of available gas is sufficient for gas detection with the FET sensor. FIG. 2 illustrates a schematic description.

Gas diffusion can be limited both by a small orifice as a diffusion limiter 16 and by a diffusion-limiting membrane that also protects the system well against dust. An advantageous embodiment of this principle is illustrated in FIG. 5. Illustrated here is the region of the gas diffusion gap 16 in a hybrid flip-chip structure for a gas sensor. A depression is made in the carrier material of the gas-sensitive gate, in which the filter material 18 is then deposited. This lengthens the diffusion gap 16. Gas diffusion is then limited by the first region of the gas diffusion gap 16. All interfering gas components are almost completely removed from the reduced amount of gas by the filter material 18, and the purified gas then reaches the detection layer 20.

The two embodiments may be used for cross sensitivities to NOx, NH$_3$, alcohols, or ketones, which represent important interfering gases for solid state gas sensors. Very effective adsorption filters are obtainable for these gases. In addition, multiple layers of activated charcoal filters can be used. For example, there are activated charcoal filters impregnated with acidic materials that adsorb basic NH$_3$ very well, and filters impregnated with alkaline materials that bind acidic NO$_2$ very well.

Moisture-adsorbing filter layers may be used, for example like silica gel, to compensate for humidity variations. The objective is not the complete removal of moisture, but the use of the filter layer as a buffer that can also emit moisture to smooth out the moisture variations interfering with gas detection.

Although the present invention has been illustrated and described with respect to several preferred embodiments thereof, various changes, omissions and additions to the form and detail thereof, may be made therein, without departing from the spirit and scope of the invention.

What is claimed is:

1. A method for increasing the selectivity of an FET-based gas sensor having a filter permeable to a target gas and which adsorbs gases on a surface of the filter that cause cross sensitivities to the target gas, where the filter is disposed between a gas mixture to be detected and a sensing element of the gas sensor, and where the filter comprises fabric-like activated charcoal, the method comprising the step of heating the sensor to a temperature at which the adsorbed gases are driven off the filter surface to thereby regenerate the filter.

2. A method for increasing the selectivity of an FET-based gas sensor having a filter permeable to the target gas and which adsorbs gases on a surface of the filter that cause cross sensitivities to the target gas, where the filter is disposed between a gas mixture to be detected and a sensing element of the gas sensor, the method comprising the step of reducing diffusion of the gas mixture to the filter by a predetermined amount that delays saturation of the filter by a predetermined time period.

3. The method of claim 1, where an operating temperature of the gas sensor is in the range between room temperature and about 100° C.

4. The method of claim 1, where the filter is positioned at a predetermined physical distance from the sensing element.

5. The method of claim 1, where the fabric-like activated charcoal material comprises viscose cellulose produced by carbonization.

6. The method of claim 1, where the filter physically absorbs gases on a surface of the filter that cause cross sensitivities to the target gas.

7. The method of claim 1, where the step of heating the sensor comprises the step of heating both the filters and the sensing element.

8. The method of claim 1, where the step of heating the sensor is carried out at a temperature of 100° C. above the operating temperature of the sensor.

9. The method of claim 1, where the step of heating the sensor is carried out in a temperature range of about 150-300° C.

10. The method of claim 1, where the step of heating the sensor is controlled automatically.

11. The method of claim 2, where the step of reducing diffusion of the gas mixture is carried out by one of the steps of providing an aperture in a gas-tight sensor housing, by providing a gas-permeable membrane in the gas sensor, and by providing a diffusion gap in the gas sensor.

12. The method of claim 1, where the filter comprises multiple layers of the fabric-like activated charcoal.

13. The method of claim 1, where the filter is impregnated with acidic materials or alkaline materials.

14. The method of claim 1, where the filter comprises a buffers for moisture.

15. The method of claim 1, where an output signal from the gas sensor is used to control a duration of the step of heating.

16. The method of claim 1, where an output signal from the gas sensor is used during the step of heating to monitor the regeneration of the filter.

17. An FET gas sensor, comprising:
a filter permeable to a target gas and which adsorbs gases on a surface of the filter;
a sensing element, where the filter is disposed between a gas mixture to be detected and the sensing element; and
a heater that heats the sensor and the filter to a temperature at which the absorbed gases are driven off the filter surface to thereby regenerate the filter.

18. An FET gas sensor, comprising:
a filter permeable to a target gas and which adsorbs gases on a surface of the filter;
a sensing element, where the filter is disposed between a gas mixture to be detected and the sensing element; and
an aperture in a gas-tight housing or a diffusion gap in the gas sensor for reducing an amount of diffusion of the gas mixture.

19. The FET gas sensor of claim 17, where the filter comprises activated charcoal.

20. An FET gas sensor, comprising:
an activated charcoal filter that is permeable to a target gas and which adsorbs non-target gases on a surface of the filter;
a gas sensing element, where the filter is disposed between a gas mixture to be detected and the sensing element; and
an aperture in a gas-tight housing or a diffusion gap in the gas sensor for reducing an amount of diffusion of the gas mixture that reaches the filter.

21. The method of claim 2, where the step of reducing diffusion of the gas mixture is carried out by one of the steps of providing an aperture in a gas-tight sensor housing or by providing a diffusion gap in the gas sensor.

* * * * *